US00RE34935E

United States Patent [19]

Rossey et al.

[11] E Patent Number: Re. 34,935

[45] Reissued Date of Patent: May 9, 1995

[54] METHOD FOR PREPARING (+)-(2S,3S)-3-HYDROXY-2-(4-METHOXY-PHENYL)-2,3-DIHYDRO-5H-1,5-BENZO-THIAZEPINE-4-ONE AND CHLORINATED DERIVATIVES THEREOF

[75] Inventors: Guy Rossey, Voisins-Le-Bretonneux; Isaac Chekroun, Epinay; Antonio Ugolini, Le Pecq; Alexander Wick, St. Nom La Breteche; Bernard Gerin; Andre Bourbon, both of Mantes La Jolie; Jean-Baptiste Graux, Mantes La Ville, all of France

[73] Assignee: Synthelabo, Robinson, France

[21] Appl. No.: 53,855

[22] Filed: Apr. 29, 1993

Related U.S. Patent Documents

Reissue of:

[64] Patent No.: 5,102,998
Issued: Apr. 7, 1992
Appl. No.: 426,285
Filed: Oct. 24, 1989

U.S. Applications:

[63] Continuation-in-part of Ser. No. 408,042, Sep. 14, 1989, Pat. No. 5,013,835.

[30] Foreign Application Priority Data

Jan. 11, 1989 [FR] France ..... 89 00246

[51] Int. Cl.[6] ..... C07D 267/02
[52] U.S. Cl. ..... 540/491
[58] Field of Search ..... 540/491

[56] References Cited

U.S. PATENT DOCUMENTS

| | | | |
|---|---|---|---|
| 4,416,819 | 11/1983 | Nagao et al. | 260/293.3 B |
| 4,420,628 | 12/1983 | Inoue et al. | 560/17 |
| 4,438,035 | 3/1984 | Gaino et al. | 260/239.3 B |
| 4,552,695 | 11/1985 | Igarashi et al. | 260/239.3 B |
| 4,885,375 | 5/1989 | Wynberg et al. | 549/557 |
| 5,008,434 | 4/1991 | Rossey et al. | 560/17 |
| 5,013,835 | 5/1991 | Rossey et al. | 560/491 |

FOREIGN PATENT DOCUMENTS

| | | |
|---|---|---|
| 0154838 | 9/1985 | European Pat. Off. . |
| 61-145159 | 7/1986 | Japan . |
| 61-145160 | 7/1986 | Japan . |
| 61-145174 | 7/1986 | Japan . |

OTHER PUBLICATIONS

Kugita et al, "Synthesis of 1,5-Benzothiazepine Derivatives", Chem. Pharm. Bull, vol. 18, 2028-2037 (1970).

Hashiyama et al., "Reaction of 3-Phenylglycidic Esters" Part 2, J. Chem. Soc. Perkin. Trans. 1:421-427, (1985).

*Primary Examiner*—Nicholas Rizzo
*Attorney, Agent, or Firm*—Jacobson, Price, Holman & Stern

[57] ABSTRACT

2-Aminothiophenol is reacted with methyl (−)-(2R,3S)-2,3-epoxy-3-(4-methoxyphenyl)propionate, and the intermediate methyl (2S,3S)-3-[(2-aminophenyl)thio]-2-hydroxy-3-(4-methoxyphenyl)propionate is cyclized in the presence of methanesulfonic acid, in the same vessel and without isolating said intermediate product, using e.g. chlorobenzene as a solvent.

6 Claims, No Drawings

METHOD FOR PREPARING (+)-(2S,3S)-3-HYDROXY-2-(4-METHOXYPHENYL)-2,3-DIHYDRO-5H-1,5-BENZOTHIAZEPINE-4-ONE AND CHLORINATED DERIVATIVES THEREOF

Matter enclosed in heavy brackets [ ] appears in the original patent but forms no part of this reissue specification; matter printed in italics indicates the additions made by reissue.

*This application is a continuation-in-part of application Ser. No. 07/408,042, filed Sep. 14, 1989, now U.S. Pat. No. 5,013,835.*

The subject of the present invention is a method for preparing (+)-(2S,3S)-3-hydroxy-2-(4-methoxyphenyl-2,3-dihydro-5H-1,5-benzothiazepine-4-one, bearing optionally a chlorine atom on the aromatic ring.

These optically pure compounds are synthetic intermediates of compounds with therapeutic activities, such as (+)-(2S,3S)-3-acetyloxy-5-(2-dimethylaminoethyl)-2-(4-methoxyphenyl)-2,3-dihydro-5H-1,5-benzothiazepine-4-one and its chlorinated derivatives.

The reaction scheme is shown on the following page. In the formulae, X denotes hydrogen or chlorine.

The first step comprises reacting a 2-aminothiophenol derivative of general formula II with methyl (−). (2R,3S)-2,3-epoxy-3-(4-methoxyphenyl)propionate of formula III. A methyl (2S,3S)-3-[(2-aminophenyl)thio]-2-hydroxy-3-(4-methoxyphenyl)propionate derivative of general formula IV is obtained via opening the epoxide ring.

The second step comprises the cyclization of this compound in the presence of an acid.

The reaction principles of each of the two steps are well known.

They are found, for example, in Chem. Pharm. Bull., 18, 2028–2037 (1970), where the ester of formula III is used in racemic form. The first step necessitates several hours of heating to 150°–160° C., and after separation and purification of the ester of formula IV, the second step is performed by hydrolyzing this ester and cyclizing the acid obtained in the presence of sulfuric or acetic acid, in refluxing xylene.

U.S. Pat. No. 4,416,819 describes the first step, where the (racemic) ester of formula III reacts with the aminothiophenol (II) in toluene after six hours of heating at reflux.

Japanese Patent Application 145160/1986, which describes the synthesis of the optically pure ester of formula III, likewise.

Scheme

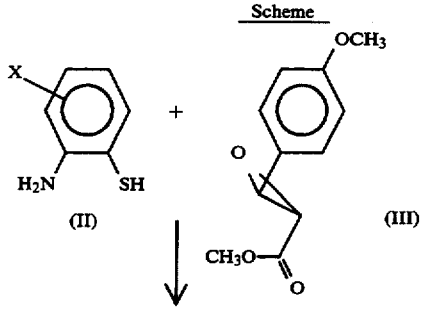

-continued

Scheme

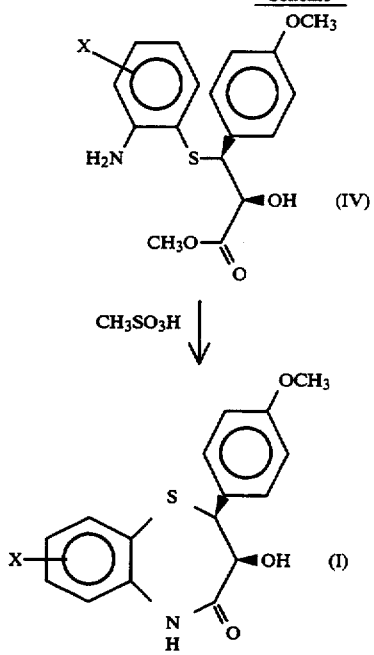

describes the reaction of the latter with aminothiophenol of formula II, under toluene reflux for 10 hours.

Finally, European Patent Application 0154838 describes among others a method that combines the two steps. The reactions are performed without solvent, requiring 16 hours of heating to 160° C., and furnishing a mixture of optical isomers of the final compound and is intermediate.

Thus it is clear that none of the known methods are suitable for economic industrial manufacture of the compounds of formula I, for various reasons: poor yields, elevated temperatures, the need to purify the intermediate and/or final compounds, and long reaction times.

The present invention therefore proposes a method that overcomes the disadvantages of the known art, and affords the following advantages:

- the two reaction steps can be performed in the one and same reactor, so that emptying and cleaning it between the two steps, or using a second reactor, is unnecessary (for reasons of convenience, the two steps can be performed in separate reactors, but anyway it is not necessary to isolate the intermediate ester);
- the total yield is high compared with the yields of the known methods;
- energy consumption is reduced, in particular during the first step;
- the reaction times are short; and
- the final compound is pure.

The operating conditions of the method according to the invention, which make it possible to attain all the advantages listed above, are described below.

The starting ester of formula III is used in optically pure form. It is described in Japanese Patent Applications 145159/1986, 145160/1986 and 145174/1986.

The possibility of carrying out the two steps of the reaction in the same vessel, without evacuation or intermediate transfer to another vessel, is due to the selection of a unique solvent which is highly suitable for each of the steps.

Specific solvents for each of the two steps are naturally already known (dichloroethane, toluene, xylene, etc.), but they are different for each step and so do not permit the entire method to take place within the same reactor. The solvents to be used according to the invention are chlorinated organic solvents having a boiling point of more than 70° C. Examples of suitable solvents are 1,2,3-trichloropropane, dichlorobenzenes and, preferably, chlorobenzene.

These solvents are not only—and unexpectedly—highly favorable to a good overall yield, but further/more they are so efficient that the first step necessitates heating only for startup, because the exothermic nature of the reaction is sufficient for it to be maintained without adding external energy. This particular feature was entirely unforeseeable, because it had never been found with other solvents.

Additionally, the use of these solvents promotes the threoerythro selectivity of the first step. With other solvents, it is in fact found that an unfavorable mixture of diastereoisomers of formula IV is obtained.

Another particular feature of the invention is due to the catalyst used in the second step. While it is known that cyclization takes place better in an acid medium (sulfuric or acetic), the catalyst to be used according to the invention is selected from methanesulfonic acid, phosphoric acid, trifluoroacetic acid, trifluoromethanesulfonic acid, perchloric acid, paratoluenesulfonic acid. The preferred catalyst is methanesulfonic acid.

These acids, which make it possible to obtain an excellent yield of the cyclized compound (I), are simple to add to the reaction medium as soon as the first step is completed.

The following examples provide a detailed illustration of the method according to the invention.

EXAMPLE 1

In an enameled, 25-liter reactor purged with nitrogen, are introduced 3 kg of methyl(−)-(2R,3S)-2,3-epoxy-3-(4-methoxyphenyl)propionate and 10 l of chlorobenzene, and the mixture is heated to 100° C. Heating is stopped, and a solution of 1900 g of 2-aminothiophenol in 1.51 of chlorobenzene is introduced in the space of 30 minutes, so as not to allow the temperature to exceed 120° C., and 3.5 l of chlorobenzene is also added to rinse the inlet funnel and the tubing.

The temperature is kept at approximately 115° C. for a further 30 minutes, and then 37.5 ml of methanesulfonic acid is added, and the mixture is heated at reflux for 8 hours, with elimination of a mixture of methanol and chlorobenzene by distillation, in order not to allow the temperature to drop below 132° C. (the boiling point of chlorobenzene).

The heating is stopped; the mixture is allowed to return to 20° C.; it is chilled to 5° C. for one hour; and the crystals formed are filtered, rinsed with chlorobenzene, and are dried in a vacuum at 100° C.

A yield of 3463 g of pure (+)-(2S,3S)-3-hydroxy-2-(4-methoxyphenyl)-2,3-dihydro-5H-1,5-benzothiazepine-4-one is obtained. Melting point: 200.3°-201.8° C. $[\alpha]_D^{20} = +114°$ (c=0.1; DMF).

EXAMPLE 2

In a 1 liter flask under an argon atmosphere are introduced 50 g of methyl (−)-(2R,3S)-2,3-epoxy-3-(4-methoxyphenyl)propionate and 350 ml of dichlorobenzene (a commercial mixture of o-, m- and p-isomers) and the mixture is heated at 115° C. Then, in the space of 30 minutes, so as not to allow the temperature to exceed 120° C., 31.8 g of 2-aminothiophenol are introduced.

The temperature is kept at 120° C. for a further 30 minutes, and then 0.62 ml of methanesulfonic acid is added, and the mixture is heated at 150° C. for 3 hours (the reaction is completed after 2 hours).

The mixture is allowed to cool; it is chilled to 5° C. for one hour; and the crystals are filtered and washed with dichlorobenzene and dried in vacuo. 49.5 g of pure (+)-(2S,3S)-3-hydroxy-2-(4-methoxyphenyl)-2,3-dihydro-5H-1,5-benzothiazepine-4-one are obtained. Melting point: 203°-204° C.

EXAMPLE 3

18.8 g of 2-aminothiophenol are added dropwise to a solution of 30 g of methyl(−)-(2R,3S)-2,3-epoxy-3-(4-methoxyphenyl)propionate in 200 ml of 1,2,3-trichloropropane at 110°-115° C. After 30 minutes 0.35 g of methanesulfonic acid is added, and the mixture is heated at 145°-150° C. for 6 hours. The mixture is allowed to cool, then chilled and filtered; the crystals are washed with 1,2,3-trichloropropane, and dried in vacuo at 50° C.

33.8 g of pure (+)-(2S,3S)-3-hydroxy-2-(4-methoxyphenyl)-2,3-dihydro-5H-1,5-benzothiazepine-4-one are obtained. Melting point: 202.8°-204.1° C.

EXAMPLE 4

In the same way as in Example 1, the reaction between 2-amino-5-chlorothiophenol and methyl (−)-(2R,3S)-2,3-epoxy-3-(4-methoxyphenyl)propionate affords (+)-(2S,3S)-8-chloro-3-hydroxy-2-(4-methoxyphenyl)-2,3-dihydro-5H-1,5-benzothiazepine-4-one. Melting point: 237°-241° C. $[\alpha]_D^{20} = +91.9°$ (c=0.1; DMF).

We claim:

1. A method for preparing a compound of the general formula (I)

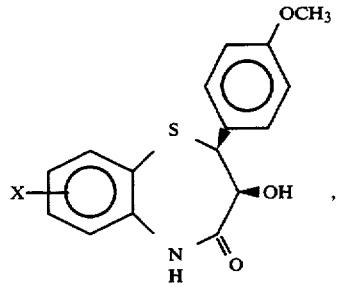

(I)

wherein X is hydrogen or chlorine, said method consisting essentially of:

reacting a compound of the general formula (II)

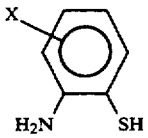

(II)

with a compound of formula (III) in optically pure levorotatory form

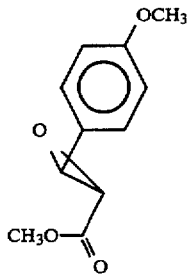

(III)

to obtain an intermediate compound of general formula (IV)

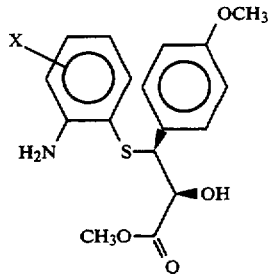

(IV)

[; and then,]

; and then, without isolating said intermediate, cyclizing the intermediate compound wherein said cyclization is effected in the presence of acid, and wherein said reacting and cyclizing steps are performed in the presence of [a solvent selected from the group consisting of chlorinated organic solvents that have boiling points greater than 70° C] *chlorobenzene.*

2. The method of claim 1, wherein X is hydrogen.

[3. The method of claim 1, wherein the solvent is chlorobenzene.]

[4. The method of claim 1, wherein the solvent is a dichlorobenzene.]

[5. The method of claim 1, wherein the solvent is 1,2,3-trichloropropane.]

6. The method of claim 1, wherein said acid is methane-sulfonic acid.

* * * * *